US00PP33982P2

(12) United States Plant Patent
Kobayashi

(10) Patent No.: US PP33,982 P2
(45) Date of Patent: Mar. 1, 2022

(54) **NEW GUINEA *IMPATIENS* PLANT NAMED 'DONGIMAGMIOR'**

(50) Latin Name: *Impatiens hawkeri*
Varietal Denomination: Dongimagmior

(71) Applicant: DUMMEN GROUP B.V., De Lier (NL)

(72) Inventor: Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/230,834

(22) Filed: Apr. 14, 2021

(51) Int. Cl.
*A01H 5/02* (2018.01)
*A01H 6/16* (2018.01)

(52) U.S. Cl.
USPC ..... Plt./318.6

(58) Field of Classification Search
USPC ..... Plt./263.1, 317, 318.1, 318.6
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct cultivar of *Impatiens* plant named 'Dongimagmior' characterized by its upright to outwardly spreading and uniformly mounding plant habit; vigorous growth habit; freely branching habit; large, glossy and dark green-colored leaves with dark red-colored midveins and lower surfaces; freely flowering habit; large flowers with cordate-shaped petals that are light purple in color with a deep red-colored blush on the banner petal; and good garden performance.

2 Drawing Sheets

Figure 1:
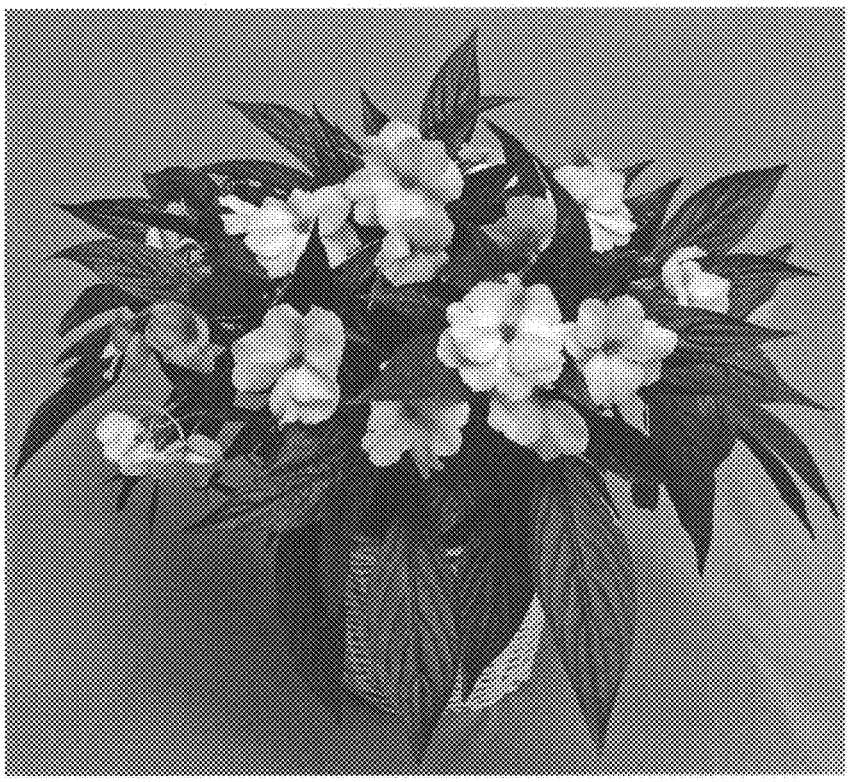

Botanical designation: *Impatiens hawkeri.*
Cultivar denomination: 'DONGIMAGMIOR'.

STATEMENT REGARDING PRIOR DISCLOSURES BY INVENTOR & APPLICANT/ASSIGNEE

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of New Guinea *Impatiens* plant, botanically known as *Impatiens hawkeri* and hereinafter referred to by the name 'Dongimagmior'.

The new *Impatiens* plant is a product of a planned breeding program conducted by the Inventor in Koka, Ethiopia and Encinitas, Calif. The objective of the breeding program is to create new freely branching and early and freely flowering New Guinea *Impatiens* plants with large attractive flowers and good garden performance.

The new *Impatiens* plant originated from a cross-pollination made by the Inventor in November, 2016 in Koka, Ethiopia of a proprietary selection of *Impatiens hawkeri* identified as code number NN15-735717-002, not patented, as the female, or seed, parent with a proprietary selection of *Impatiens hawkeri* identified as code number NN07-

001623-005, not patented, as the male, or pollen, parent. The new *Impatiens* plant was discovered and selected by the Inventor as a single flowering plant from within the progeny of the stated cross-pollination in a controlled greenhouse environment in Encinitas, Calif. in April, 2017.

Asexual reproduction of the new *Impatiens* plant by terminal vegetative cuttings in a controlled greenhouse environment in Rheinberg, Germany since June, 2017 has shown that the unique features of this new *Impatiens* plant are stable and reproduced true to type in successive generations.

SUMMARY OF THE INVENTION

Plants of the new *Impatiens* have not been observed under all possible combinations of environmental conditions and cultural practices. The phenotype may vary somewhat with variations in environmental conditions such as temperature, daylight and light intensity without, however, any variance in genotype.

The following traits have been repeatedly observed and are determined to be the unique characteristics of 'Dongimagmior'. These characteristics in combination distinguish 'Dongimagmior' as a new and distinct *Impatiens* plant:

1. Upright to outwardly spreading and uniformly mounding plant habit.
2. Vigorous growth habit.
3. Freely branching habit.
4. Large, glossy and dark green-colored leaves with dark red-colored midveins and lower surfaces.
5. Freely flowering habit.
6. Large flowers with cordate-shaped petals that are light purple in color with a deep red-colored blush on the banner petal.
7. Good garden performance.

Plants of the new *Impatiens* can be compared to plants of the female parent selection. Plants of the new *Impatiens* differ primarily from plants of the female parent selection in the following characteristics:

1. Plants of the new *Impatiens* are more vigorous than plants of the female parent selection.
2. Plants of the new *Impatiens* have larger flowers than plants of the female parent selection.
3. Flowers of plants of the new *Impatiens* are light purple in color with a deep red-colored blush on the banner petal whereas flowers of plants of the female parent selection are red in color with lavender-colored centers.

Plants of the new *Impatiens* can be compared to plants of the male parent selection. Plants of the new *Impatiens* differ primarily from plants of the male parent selection in the following characteristics:

1. Plants of the new *Impatiens* are more vigorous than plants of the male parent selection.
2. Plants of the new *Impatiens* have darker green-colored leaves than plants of the male parent selection.
3. Plants of the new *Impatiens* flower earlier than plants of the male parent selection.
4. Flowers of plants of the new *Impatiens* are light purple in color with a deep red-colored blush on the banner petal whereas flowers of plants of the male parent selection are white in color.

Plants of the new *Impatiens* can be compared to plants of *Impatiens hawkeri* 'Doimmalaven', disclosed in U.S. Plant Pat. No. 30,744. In side-by-side comparisons, plants of the new *Impatiens* differ primarily from plants of 'Doimmalaven' in the following characteristics:

1. Plants of the new *Impatiens* are more vigorous than plants of 'Doimmalaven'.
2. Plants of the new *Impatiens* have darker green-colored leaves than plants of 'Doimmalaven'.
3. Plants of the new *Impatiens* have smaller flowers than plants of 'Doimmalaven'.
4. Flowers of plants of the new *Impatiens* are light purple in color with a deep red-colored blush on the banner petal whereas flowers of plants of 'Doimmalaven' are purple to red purple in color with white-colored centers.

Plants of the new *Impatiens* can also be compared to plants of *Impatiens hawkeri* 'Moorea', disclosed in U.S. Plant Pat. No. 9,147. In side-by-side comparisons, plants of the new *Impatiens* differ primarily from plants of 'Moorea' in the following characteristics:

1. Plants of the new *Impatiens* are more vigorous than plants of 'Moorea'.
2. Plants of the new *Impatiens* have larger flowers than plants of 'Moorea'.
3. Flowers of plants of the new *Impatiens* are light purple in color with a deep red-colored blush on the banner petal whereas flowers of plants of 'Moorea' are white in color.

BRIEF DESCRIPTION OF THE PHOTOGRAPHS

The accompanying colored photographs illustrate the overall appearance of the new *Impatiens* plant showing the colors as true as it is reasonably possible to obtain in colored reproductions of this type. Colors in the photographs may differ slightly from the color values cited in the detailed botanical description which accurately describe the colors of the new *Impatiens* plant.

The photograph on the first sheet (FIG. 1) is a side perspective view of a typical flowering plant of 'Dongimagmior' grown in a container.

Figure 2:
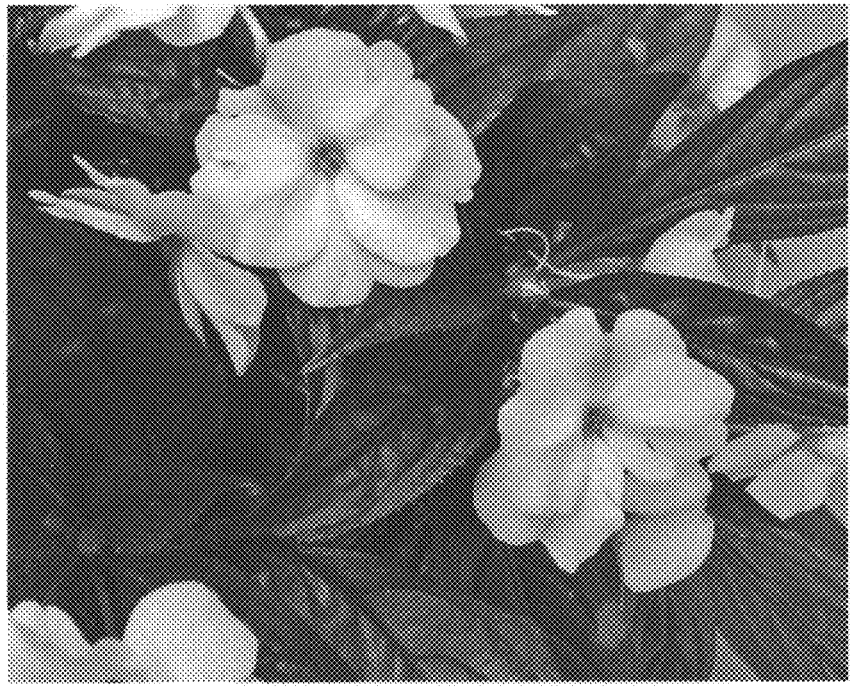

The photograph on the second sheet (FIG. 2) is a close-up view of a typical flowering plant of 'Dongimagmior'.

DETAILED BOTANICAL DESCRIPTION

The aforementioned photographs and following observations, measurements and values describe plants grown during the summer in 16.5-cm containers in a polyethylene-covered greenhouse in Encinitas, Calif. and under cultural practices typical of commercial New Guinea *Impatiens* production. During the production of the plants, day temperatures averaged 25° C., night temperatures averaged 20° C. and light levels ranged from 4,000 to 4,500 lux. Plants were 14 weeks old when the photographs and description were taken. In the following description, color references are made to The Royal Horticultural Society Colour Chart, 2015 Edition, except where general terms of ordinary dictionary significance are used.

Botanical classification: *Impatiens hawkeri* 'Dongimagmior'.

Parentage:

*Female, or seed, parent.*—Proprietary selection of *Impatiens hawkeri* identified as code number NN15-735717-002, not patented.

*Male, or pollen, parent.*—Proprietary selection of *Impatiens hawkeri* identified as code number NN07-001623-005, not patented.

Propagation:

*Type.*—By terminal vegetative cuttings.

*Time to initiate roots, summer and winter.*—About five to seven days at day temperatures about 27° C. and night temperatures about 20° C.

*Time to produce a rooted young plant, summer and winter.*—About three weeks at day temperatures about 27° C. and night temperatures about 20° C.

*Root description.*—Fine, fibrous; typically white in color, actual color of the roots is dependent on substrate composition, water quality, fertilizers, substrate temperature and age of roots.

*Rooting habit.*—Freely branching; dense.

Plant description:

*Plant and growth habit.*—Upright to outwardly spreading and uniformly mounding plant habit; broad inverted triangle in overall shape; freely branching habit; bushy and dense appearance; vigorous growth habit and moderate to rapid growth rate; strong and sturdy plants.

*Plant height.*—About 29.5 cm.

*Plant diameter.*—About 48 cm.

Lateral branch description:

*Branching habit.*—Freely branching with about five to six primary lateral branches each with multiple secondary branches.

*Length.*—About 25.5 cm.

*Diameter.*—About 1 cm to 1.5 cm.

*Internode length.*—About 6 cm to 7 cm.

*Strength.*—Strong, flexible.

*Aspect.*—Initially upright to about 45° from vertical.

*Texture and luster.*—Smooth, glabrous; glossy.

*Color, developing.*—Close to 187A.

*Color, developed.*—Close to 146A heavily overlain with close to 183A.

Leaf description:

*Arrangement*.—Typically in whorls or opposite; simple; leaves are durable.

*Length*.—About 12.5 cm.

*Width*.—About 4.5 cm.

*Shape*.—Obovate to elliptic.

*Apex*.—Long acuminate.

*Base*.—Cuneate to attenuate.

*Margin*.—Serrate with ciliation.

*Texture and luster, upper surface*.—Smooth, glabrous; coriaceous; glossy.

*Texture and luster, lower surface*.—Smooth, glabrous; coriaceous; moderately glossy.

*Venation pattern*.—Pinnate; arcuate.

*Color*.—Developing leaves, upper surface: Darker green than 147A. Developing leaves, lower surface: Close to 183B. Fully expanded leaves, upper surface: Slightly more green than N189A; midvein, close to 183A and lateral venation, close to N189A. Fully expanded leaves, lower surface: Close to 183A; midvein and lateral venation, close to 183A.

*Petiole length*.—About 4 cm to 6 cm.

*Petiole diameter*.—About 4 mm to 5 mm.

*Petiole texture and luster, upper and lower surfaces*.—Smooth, glabrous; glossy.

*Petiole color, upper surface*.—Close to 183A to 183B.

*Petiole color, lower surface*.—Close to 183A.

Flower description:

*Flower type and flowering habit*.—Large single axillary flowers that are rounded in shape; freely flowering habit, typically about five to six flower buds and opened flowers per lateral branch; flowers are flat and positioned above and beyond the foliar plane, flowers typically face mostly upright to outwardly.

*Flower longevity*.—Flowers typically last about four to seven days on the plant under greenhouse conditions; petals self-cleaning, gynoecium persistent.

*Fragrance*.—None detected.

*Natural flowering season*.—Year-round under greenhouse conditions; in the garden, flowering from spring until fall in California; early flowering habit, plants typically begin flowering about ten weeks from unrooted cuttings.

*Flower buds*.—Length: About 1.2 cm. Diameter: About 7.5 mm. Shape: Ovoid. Texture and luster: Smooth, glabrous; glossy. Color: Close to 183A.

*Flower diameter*.—Large, about 7.5 cm by 8 cm.

*Flower depth*.—About 1 cm.

*Petals*.—Quantity and arrangement: Five per flower in a single whorl with one banner petal, two lateral petals and two lower petals. Length, banner petal: About 3.3 cm. Length, lateral petals: About 3.7 cm. Length, lower petals: About 3.9 cm. Width, banner petal: About 5.75 cm. Width, lateral petals: About 4.3 cm. Width, lower petals: About 4.3 cm. Shape, all petals: Roughly cordate. Apex, all petals: Emarginate. Base, all petals: Cuneate. Margin, all petals: Entire, slightly undulate. Texture and luster, all petals, upper and lower surfaces: Smooth, glabrous; slightly glossy; iridescent. Color, banner petals: When opening, upper surface: Close to 69D; towards the base and midvein, close to 60A; upper blotch, close to 60A. When opening, lower surface: Close to 76C; midvein, close to 183A. Fully opened, upper surface: Close to 76C to 76D; towards the base and at the apex, close to 60A; midvein, close to 60A; upper blotch, close to 60A; main color becoming closer to 76D with subsequent development. Fully opened, lower surface: Close to 76C to 76D; midvein, close to 183A; main color becoming closer to 76D with subsequent development. Color, lateral and lower petals: When opening, upper surface: Close to 69D; towards the base and midvein, close to 60A. When opening, lower surface: Close to 76C; midvein, close to N57A. Fully opened, upper surface: Close to 76C to 76D; towards the base and at the apex, close to 60A; midvein, close to 60A; main color becoming closer to 76D with subsequent development. Fully opened, lower surface: Close to 76C to 76D; midvein, close to N57A; main color becoming closer to 76D with subsequent development.

*Sepals*.—Quantity and arrangement: Three in a single whorl; two laterals are opposite and the third modified into an elongated spur. Lateral sepal length: About 1.4 cm. Lateral sepal width: About 7 mm. Lateral sepal shape: Narrowly ovate. Lateral sepal apex: Acuminate to cuspidate. Lateral sepal base: Truncate. Lateral sepal margin: Entire, not undulate. Lateral sepal texture and luster, upper and lower surfaces: Smooth, glabrous; moderately glossy. Lateral sepal color, upper surface: Close to 148B. Lateral sepal color, lower surface: Close to 183A. Spurred sepal length (not including spur): About 1.9 cm. Spurred sepal width (proximally): About 1.5 cm. Spurred sepal shape (proximally): Broadly ovate. Spurred sepal base: Cordate. Spurred sepal margin (proximally): Entire, not undulate. Spurred sepal texture and luster (proximally), upper and lower surfaces: Smooth, glabrous; moderately glossy. Spurred sepal color (proximally), upper surface: Close to 76D. Spurred sepal color (proximally), lower surface: Close to 76C; towards the base, close to 60A; midvein, close to 60A. Spur length: About 4.5 cm. Spur diameter: At flower, about 2 mm; at apex, less than 1 mm. Spur shape: Acicular, curved. Spur texture and luster: Smooth, glabrous; moderately glossy. Spur color: Close to 144B to 144C.

*Peduncles*.—Length: About 5 cm. Diameter: About 2 mm. Angle: About 45° to 90° from vertical. Strength: Strong; flexible. Texture and luster: Smooth, glabrous; glossy. Color: Between 144A and 146A.

*Reproductive organs*.—Stamens: Quantity: Five fused at anthers; filaments free. Filament length: About 3.5 mm. Filament color: Close to 158A. Anther length: About 3 mm. Anther shape: Oblong. Anther color: Close to N155B. Pollen amount: Scarce. Pollen color: Close to 158A. Pistils: Quantity per flower: One. Pistil length: About 4.5 mm. Stigma shape: Crested. Stigma color: Close to 144A. Style length: About 3.75 mm. Style color: Close to 144A. Ovary color: Close to 144A.

*Seeds and fruits*.—To date, seed and fruit production has not been observed on plants of the new *Impatiens*.

Pathogen & pest resistance: To date, plants of the new *Impatiens* have not been observed to be resistant to pathogens and pests common to *Impatiens* plants.

Garden performance: Plants of the new *Impatiens* have been observed to have good garden performance and tolerate temperatures ranging from about 5° C. to about 40° C.

It is claimed:

1. A new and distinct *Impatiens* plant named 'Dongimagmior' as illustrated and described.

* * * * *